(12) United States Patent
Labow et al.

(10) Patent No.: US 6,833,241 B2
(45) Date of Patent: Dec. 21, 2004

(54) MAMMARY GLAND CHEMOKINE

(75) Inventors: Mark A. Labow, Westfield, NJ (US);
Craig Stephen Mickanin, Basking Ridge, NJ (US); Umesh Bhatia, Los Gatos, CA (US)

(73) Assignee: Novartis, East Hanover, NJ (US)

( * ) Notice: Subject to any disclaimer, the term of this patent is extended or adjusted under 35 U.S.C. 154(b) by 0 days.

(21) Appl. No.: 09/813,492

(22) Filed: Mar. 21, 2001

(65) Prior Publication Data

US 2002/0009735 A1 Jan. 24, 2002

Related U.S. Application Data

(60) Provisional application No. 60/191,654, filed on Mar. 23, 2000.

(51) Int. Cl.[7] .................... G01N 33/48; C12Q 1/68
(52) U.S. Cl. ................ 435/6; 435/4; 436/63; 436/64; 536/23.5
(58) Field of Search .............. 435/4, 6; 436/63, 436/64; 536/23.5, 23.4

(56) References Cited

U.S. PATENT DOCUMENTS 5,527,676 A * 6/1996 Vogelstein et al.
6,153,387 A * 11/2000 Band
6,306,653 B1 * 10/2001 Papsidero et al.

FOREIGN PATENT DOCUMENTS

| WO | 98/23750 | 6/1998 |
| WO | 99/06439 | 2/1999 |
| WO | 99/36540 | 7/1999 |
| WO | 00/38713 | 7/2000 |
| WO | 01/07482 A1 | 2/2001 |

OTHER PUBLICATIONS

Coghlan, J. P. et al., Analytical Biochemistry, 149: 1–28, 1985.*

Pan, Junliang et al., "Cutting Edge: A Novel Chemokine Ligand for CCR10 And CCR3 Expressed by Epithelial Cells in Mucosal Tissues," Journal of Immunology, vol. 165, pp. 2943–2949 (2000).

Wang, Wei et al., "Identification of a Novel Chemokine (CCL28), which Binds CCR10 (GPR2)," The Journal of Biological Chemistry, vol. 275(29), pp. 22313–22323 (2000).

"NCI Award Summary, Identifying No:1R43CA80576–01A2".

"GenBank Acc. No. ACO25457 Summary".

* cited by examiner

Primary Examiner—Alana M. Harris
Assistant Examiner—Anne L. Holleran
(74) Attorney, Agent, or Firm—Diane Tso; Regina Bautista

(57) ABSTRACT

The present invention provides various methods for utilizing a polypeptide encoding a chemokine (MEC) and a polypeptide translated therefrom. The MEC chemokine is underexpressed in tumors, making the chemokine a useful marker for diagnosis and prognosis of adverse bodily reactions.

7 Claims, 2 Drawing Sheets

```
TAGATACCCTGAACACCTCCCAGGGCGGGGCCACCTGGCTTACTTTTCCTCTGCACTTTCTCTGTGCCCAAGGACACCTT        80

MetGlnGlnArgGly
TAGCCTCATTTCCTGATCGAACAGCCTCACTTGTGTTGCTGTCAGTGCCAGTAGGGCAGGCAGGAATGCAGCAGAGAGGA       160

LeuAlaIleValAlaLeuAlaValCysAlaAlaLeuHisAlaSerGluAlaIleLeuProIleAlaSerSerCysCysTh
CTCGCCATCGTGGCCTTGGCTGTCTGTGCGGCCCTACATGCCTCAGAAGCCATACTTCCCATTGCCTCCAGCTGTTGCAC       240 rGluValSerHisHisIleSerArgArgLeuLeuGluArgValAsnMetCysArgIleGlnArgAlaAspGlyAspCysA
GGAGGTTTCACATCATATTTCCAGAAGGCTCCTGGAAAGAGTGAATATGTGTCGCATCCAGAGAGCTGATGGGGATTGTG       320 spLeuAlaAlaValIleLeuHisValLysArgArgArgIleCysValSerProHisAsnHisThrValLysGlnTrpMet
ACTTGGCTGCTGTCATCCTTCATGTCAAGCGCAGAAGAATCTGTGTCAGCCCGCACAACCATACTGTTAAGCAGTGGATG       400

LysValGlnAlaAlaLysLysAsnGlyLysGlyAsnValCysHisArgLysLysHisHisGlyLysArgAsnSerAsnAr
AAAGTGCAAGCTGCCAAGAAAAATGGTAAAGGAAATGTTTGCCACAGGAAGAAACACCATGGCAAGAGGAACAGTAACAG       480 gAlaHisGlnGlyLysHisGluThrTyrGlyHisLysThrProTyr
GGCACATCAGGGGAAACACGAAACATACGGCCATAAAACTCCTTATTAGAGAGTCTACAGATAAATCTACAGAGACAATT       560

CCTCAAGTGGACTTGGCCATGATTGGTTGTAAGTTTATCATCTGAATTCTCCTTATTGTAGACAACAGAACAAAACAAAA       640
TATTGGTTTTTAAAAAATGAACAATTGTGCGGTATGCAAATGTAGCCAATAATATACTCAAACTCCTGGGCTCAAGCGAT       720
CCTCCCACCTTAGCCTCCCAAAGTACTGGGATTATAGGTGTGAGCCACAGTGCCTGGCCTAATTATTTTCTTGTGATCAA       800
ATTCAGGTTTAATGTTTTTGGTTAAGAATTTCCTACGTGAATTCGTGTACTTATTTTGTCATTTAGAGTTCATAAATATT       880
AGGGTTTATTTTCTAAATAGAATAGTTTAAACTAAATATAACTTCAAAACGTCTAGTTTGAGTAGCTACCGTTGTTTGGA       960
TTGAAATTTTCTGATACTGAAAAGAACAAAAAGCCTGCCTTTCTGCCCAGAACCTTTTGCCTCCCCCAGTCAGTTCTTGG      1040
AGCAGCACTAGTTAGGGGCCCAGAGTTCGGCCTTCTGTGTGGTGATTTTACGCTCTGCCTAAACAAGGAGCCTACATCTT      1120
TTAGCTCCTATTCCACCCTTCTCACACGTTTTTGTTGTTGTTTGGTTGTTTTTTTTGAGACAGAGTCTCACTCTGTTGC      1200
CCAGGCTGGAGTGCAGTGGCACAATCTCGGCTCATTGCAACCTCCGCCTCCCGCGTTCAAGTGATTCTCTTGCCTCAGCC      1280
TCCCAAGTAACTGATATTACAGGCGCCCAGCCACCACACCCCGCTGATTTTTGTATTTTTAGTAGAGACGGGGTTTTCCC      1360
ACGTTGGCCGGGCTGGTCTCAAACTCTTGACCTCAAGTGAACCACCCGCCTGTGCCTCCCAAAGTGCTGGAATTACCAGC      1440
GTGAGCCACCATGCCGGGCTCACACGTTTGAGTTGATACCATTGTGCCATTCCTCTTTTGGCCTCTTTTTTGTCCATAGA      1520
GGCTTCAAGATAGATAGGTAAGAGCCCAGTAGTGTTCATAAGAAGCCAATAGAGAGCAGGAGCCACTTTATCAGGTGGCA      1600
GGTGTCCCGGGCCTCCCTGCTGGCTAGTCCCAAGCGGTGGTGTTGCCAGGATGTCTTGGAGGTGATAATGGGACACACAG      1680
AGGCACTGAGTCTCCATAGGTTAAAATGCCACCAAAACTGGCCTTTGCCTAATATCCCTCATTGACTATTTAGCATTTAA      1760
TTTATTTATTTTCCTGACATTTCTGCAAGCTTTGTATTTATATTTCCACTTTATAGATGAGGAAATTTGAGGCTCTTAGA      1840
GGTAAAATGACTTGCCCAGGTCACACAGGAAGTGGCAGAGACAAGCTTTTTAAATAAGAAAAAATTAATAAAATATAATA      1920
TGAGAGTAACTTAAAATATTAATAAACCACAATTTTAAATTAATTAACCGTGATAACCAACATTAATAAAAGTTAAGATA      2000
CCAAAAAAAAAAAAAAA
```

FIG. 1

```
            1
MEC       MQQRG....L AIVALAVCAA LHASEA.ILP IASSCCTEVS HH.ISRRLLE
hTECK     ""MKGPPTFC SLLLLSLLLS PDPTAAFLLP PSTACCTQLY RKPLSDKLLR
Exodus-1  ""MACGGKRL LFLALAWVLL AHLCSQAEAA SNYDCCLSYI QTPLPSRAI.

51
MEC       RVNMCRIQRA DGDCDLAAVI LHVKRR.RIC VSPHNHTVKQ WMKVQAAKKN
hTECK     KVIQVELQEA DGDCHLQAFV LHLAQR.SIC IHPQNPSLSQ WFEHQERKLH
Exodus-1  .VGFTR.QMA DEACDINAII FHTKKRKSVC ADPKQNWVKR AVNLLSLRVK 101
MEC       G...KGNVCH RKKHHGKRNS HRAHQGKHET YGHKPY
hTECK     GTLPKLNFGM LRKMG""""" """""""""" """"""
Exodus-1  KM"""""""" """""""""" """""""""" """"""
```

FIG. 2

SEQUENCE LISTING

<160> NUMBER OF SEQ ID NOS: 2

<210> SEQ ID NO 1
<211> LENGTH: 2017
<212> TYPE: DNA
<213> ORGANISM: HUMAN

<400> SEQUENCE: 1

```
tagataccct gaacacctcc cagggcgggg ccacctggct tacttttcct ctgcactttc      60
tctgtgccca aggacacctt tagcctcatt tcctgatcga acagcctcac ttgtgttgct     120
gtcagtgcca gtagggcagg caggaatgca gcagagagga ctcgccatcg tggccttggc     180
tgtctgtgcg gccctacatg cctcagaagc catacttccc attgcctcca gctgttgcac     240
ggaggtttca catcatattt ccagaaggct cctggaaaga gtgaatatgt gtcgcatcca     300
gagagctgat ggggattgtg acttggctgc tgtcatcctt catgtcaagc gcagaagaat     360
ctgtgtcagc ccgcacaacc atactgttaa gcagtggatg aaagtgcaag ctgccaagaa     420
aaatggtaaa ggaaatgttt gccacaggaa gaaacaccat ggcaagagga acagtaacag     480
ggcacatcag gggaaacacg aaacatacgg ccataaaact ccttattaga gagtctacag     540
ataaatctac agagacaatt cctcaagtgg acttggccat gattggttgt aagtttatca     600
tctgaattct ccttattgta gacaacagaa caaaacaaaa tattggtttt taaaaaatga     660
acaattgtgc ggtatgcaaa tgtagccaat aatatactca aactcctggg ctcaagcgat     720
cctcccacct tagcctccca aagtactggg attataggtg tgagccacag tgcctggcct     780
aattattttc ttgtgatcaa attcaggttt aatgtttttg gttaagaatt tcctacgtga     840
attcgtgtac ttattttgtc atttagagtt cataaatatt agggtttatt ttctaaatag     900
aatagtttaa actaaatata acttcaaaac gtctagtttg agtagctacc gttgtttgga     960
ttgaaatttt ctgatactga aaagaacaaa aagcctgcct ttctgcccag aaccttttgc    1020
ctcccccagt cagttcttgg agcagcacta gttagggcc cagagttcgg ccttctgtgt    1080
ggtgatttta cgctctgcct aaacaaggag cctacatctt ttagctccta ttccacccctt   1140 ctcacacgtt tttgttgttg tttggttgtt ttttttgag acagagtctc actctgttgc     1200
ccaggctgga gtgcagtggc acaatctcgg ctcattgcaa cctccgcctc ccgcgttcaa    1260
gtgattctct tgcctcagcc tcccaagtaa ctgatattac aggcgcccag ccaccacacc    1320
ccgctgattt ttgtatttt agtagagacg gggttttccc acgttggccg ggctggtctc    1380
aaactcttga cctcaagtga accacccgcc tgtgcctccc aaagtgctgg aattaccagc    1440
gtgagccacc atgccgggct cacacgtttg agttgatacc attgtgccat tcctcttttg    1500
gcctcttttt tgtccataga ggcttcaaga tagataggta agagcccagt agtgttcata    1560
agaagccaat agagagcagg agccacttta tcaggtggca ggtgtcccgg gcctccctgc    1620
tggctagtcc caagcggtgg tgttgccagg atgtcttgga ggtgataatg ggacacacag    1680
```

-continued

```
aggcactgag tctccatagg ttaaaatgcc accaaaactg gcctttgcct aatatccctc    1740
attgactatt tagcatttaa tttatttatt ttcctgacat ttctgcaagc tttgtattta    1800
tatttccact ttatagatga ggaaatttga ggctcttaga ggtaaaatga cttgcccagg    1860
tcacacagga agtggcagag acaagcttt  taaataagaa aaaattaata aaatataata   1920
tgagagtaac ttaaaatatt aataaaccac aattttaaat taattaaccg tgataaccaa    1980
cattaataaa agttaagata ccaaaaaaaa aaaaaaa                             2017
```

<210> SEQ ID NO 2
<211> LENGTH: 127
<212> TYPE: PRT
<213> ORGANISM: HUMAN

<400> SEQUENCE: 2

```
Met Gln Gln Arg Gly Leu Ala Ile Val Ala Leu Ala Val Cys Ala Ala
 1               5                  10                  15

Leu His Ala Ser Glu Ala Ile Leu Pro Ile Ala Ser Ser Cys Cys Thr
            20                  25                  30

Glu Val Ser His His Ile Ser Arg Arg Leu Leu Glu Arg Val Asn Met
         35                  40                  45

Cys Arg Ile Gln Arg Ala Asp Gly Asp Cys Asp Leu Ala Ala Val Ile
     50                  55                  60

Leu His Val Lys Arg Arg Ile Cys Val Ser Pro His Asn His Thr
 65                  70                  75                  80

Val Lys Gln Trp Met Lys Val Gln Ala Ala Lys Lys Asn Gly Lys Gly
                 85                  90                  95

Asn Val Cys His Arg Lys Lys His His Gly Lys Arg Asn Ser Asn Arg
            100                 105                 110

Ala His Gln Gly Lys His Glu Thr Tyr Gly His Lys Thr Pro Tyr
            115                 120                 125
```

MAMMARY GLAND CHEMOKINE

This application claims priority under 35 U.S.C. §119(e) from U.S. Provisional Application No. 60/191,654, filed Mar. 23, 2000, the contents of which is incorporated by reference herein in its entirety.

This invention relates to newly identified polynucleotides and polypeptides encoded by the polynucleotides that are specifically expressed in specific tissues, especially in the mammary gland tissue.

BACKGROUND OF INVENTION

Chemokines are small polypeptides which are diverse but highly related. Chemokine genes encode small secretable molecules that promote diverse biological activities. Many chemokines have proinflammatory activities and are involved in many steps in an inflammatory reaction. For example, many chemokines stimulate histamine and leukotriene release, increase adherence of target immune cells to endothelial cells and enhance binding of complement proteins. Other biological activities of chemokines include growth and control of tumor cells and angiogenesis.

Chemokines are divided into four different families including the C-X-C chemokine ($\alpha$) family and the C-C chemokine ($\beta$) family. The C-X-C and C-C chemokines typically contain four cysteine residues and are categorized by the spacing of the first two cysteine residues. In general, the C-X-C chemokines activate neutrophils and fibroblasts while the C-C chemokines act on a more diverse group of target cells. However, some chemokines from one family show characteristics of the other. Because of their diverse array of activities in regulating clinically important biological processes, chemokines are attractive targets for therapeutic intervention. Additionally, chemokines can be used as important diagnostic tools. Patients often do not manifest symptoms at early stages of disease or tumor development, making development of new diagnostic techniques important. Because chemokine gene expression is often regulated, chemokines can be useful tools for early and accurate diagnoses.

SUMMARY OF THE INVENTION

The present invention provides a method for regulating an adverse bodily reaction having the steps of providing a therapeutic composition comprising a polypeptide having the sequence of SEQ ID NO:2, and providing said therapeutic composition to the area of adverse reaction. Additionally provided is a method for detecting an adverse bodily reaction, which method has the steps of providing an antibody of a polypeptide comprising the sequence of SEQ ID NO:2 or a fragment thereof; contacting said probe to a sample of body fluid, tissue or tissue extract from a patient under a binding condition to produce a hybridized probe; and quantifying the level of bound polypeptides. The invention also provides polynucleotide probes having nucleic acid molecules of sufficient length to specifically hybridize to a nucleic acid sequence of the present invention. Such probes are suitable for diagnosis and prognosis of adverse bodily reactions, including growth of tumors.

The polynucleotides and polypeptides of the present invention are suitable as research agents and materials for discovery of treatments and diagnostics to human disease.

BRIEF DESCRIPTION OF THE FIGURES

The following figures are illustrative of embodiments of the present invention and are not meant to limit the scope of the invention thereto.

FIG. 1 depicts the cDNA sequence (SEQ ID NO:1) and corresponding amino acid sequence (SEQ ID NO:2) of the present chemokine. The protein has a leader sequence (underlined) of about 19 amino acid residues.

FIG. 2 illustrates a comparison of the amino acid sequence homology between the present chemokine (SEQ ID NO:2), CCL27, human TECK and human Exodus-1.

DETAILED DESCRIPTION OF THE INVENTION

The present invention provides a novel human chemokine of the CC family, which has the amino acid sequence of SEQ ID NO:2, as shown in FIG. 1. The amino acid sequence is encoded by the polynucleotide sequence of SEQ ID NO:1. The chemokine is highly expressed in specific tissues including mammary gland, uterus, spleen and thymus, and it is especially expressed in high levels in the mammary gland. Hereinafter the chemokine of the present invention is referred to as the mammary gland enriched chemokine, MEC, and the gene of the chemokine is referred to mec, i.e., mec encodes the polypeptide designated MEC. The polynucleotide, mec, contains an open reading frame encoding a protein of approximately 127 amino acids in length with a leader sequence of about first 19 residues. The mature protein is predicted to have about 108 amino acids in length. Mature MEC has approximately 35% and 30% amino acid homology to CCL27 and human Exodus-1, respectively.

Aside from typical proinflammatory activities expected from a chemokine, it has been found that the present chemokine is underexpressed in tumors, especially in mammary gland tumors. Accordingly, a diagnostic or prognostic test for identifying underexpression of MEC can be used to identify tumors even when the tumors are not large enough to be detectable by a conventional method, e.g., mammogram. MEC is also believed to be useful as a therapeutic agent for controlling tumors.

The mec nucleotide sequence, which encodes MEC, has many uses in techniques known in the art of molecular biology. Suitable techniques for using mec include recombinant production of MEC, generation of anti-sense RNA and DNA, production of hybridization probes, antibody, and mapping chromosome or gene. The present invention further provides for variants of the polynucleotides and polypeptides of the present invention. The variant of the polynucleotides may be a naturally occurring allelic variant of the polynucleotide or non-naturally occurring variant of the polynucleotide. Such variants include deletion variants, substitution variants and addition or insertion variants.

The mec nucleotides can be joined to a variety of other nucleotide sequences by various recombinant DNA techniques known in the art. Suitable nucleotide sequences include cloning vectors, e.g., plasmids, cosmids, lamda phage derivatives, and the like. Other suitable vectors include expression vectors, sequencing vectors, replication vectors, probe generation vectors, and the like.

As indicated above, one of the utilities for the present nucleotides is providing hybridization probes that hybridize with naturally occurring nucleotide sequences encoding the expressed chemokine. Such probes are employed to detect and identify chemokines having similar nucleotide sequences, preferably at least about 50% homology compared to the mec sequence. Hybridization probes may be labeled by a variety of known labeling groups, for example, radionucleotides, e.g., $^{32}P$ and $^{35}S$, and enzymatic labels, e.g., alkaline phosphatase. Hybridization probes can be produced by a recombinant or chemical method. For example, a present nucleotide sequence, or a derivative or fragment thereof is cloned into a vector to produce an mRNA probe that will specifically hybridize. Suitable vectors are known in the art and are commercially available. To achieve specific hybridization under a variety of conditions, such probes may include the full mec nucleotide sequence or a fragment thereof. The term a fragment of mec as used herein indicates a gene sequence that is unique for the mec sequence and is at least about 10 consecutive nucleotides in length, preferably at least about 20 consecutive nucleotides, more preferably at least about 50 consecutive nucleotides. The term specific hybridization indicates hybridizing of a molecule only to a particular nucleotide sequence under stringent conditions. Generally, highly stringent conditions are selected to be about 5° C. lower than the thermal melting point for the specific sequence at a defined ionic strength and pH. A guide to the hybridization of nucleic acids is found in Tijssen (1993) *Laboratory Techniques in Biochemistry and Molecular Biology-Hybridization with Nucleic Acid Probes* part 1 chapter 2 "Overview of principles of hybridization and the strategy of nucleic acid probe assays" Elsevier, New York.

The mec nucleotides and probes produced therefrom can also be used to construct an assay to detect diseases associated with abnormal levels of expression of MEC, e.g., tumor. Levels of mRNA encoding MEC can be assayed using any appropriate method known in the art. Suitable methods include Northern blot analysis, S1 nuclease mapping, the polymerase chain reaction (PCR), the reverse transcription polymerase chain reaction (RT-PCR) and the reverse transcription ligase chain reaction (RT-LCR). For example, the nucleotides can be labeled and added to a body fluid or tissue sample from a patient under a hybridizing condition. The hybridized sample is washed and reacted with a dye that selectively reacts with the hybridized nucleotides. The amount of reacted dye is measured to determine the level expression of mRNA corresponding to mec. If the expression level is less than the normal level, the result indicates the presence of a tumor.

The polypeptides encoded by the mec nucleotides can be used to identify the receptor for the polypeptides. The gene encoding the receptor can be identified by numerous methods known to those skilled in the art, for example, ligand panning and FACS sorting (Coligan, et al., Current Protocols in Immun., 1(2), Chapter 5, (1991)). For example, expression cloning can be used. Polyadenylated RNA is prepared from a cell responsive to MEC, and a cDNA library created from this RNA is divided into pools and used to transfect COS cells or other cells that are not responsive to MEC. Transfected cells are exposed to the labeled MEC polypeptide. The polypeptide of the present invention can be labeled by a variety of means including iodination or inclusion of a recognition site for another enzyme or an epitope tag. Following fixation and incubation, the cells are subjected to auto-radiographic analysis. Positive pools are identified and sub-pools are prepared and re-transfected using an iterative sub-pooling and re-screening process, eventually yielding a single clone that encodes the putative receptor. As an alternative approach for receptor identification, labeled ligand can be photoaffinity linked with cell membrane or extract preparations that express the receptor molecule. Cross-linked material is resolved by PAGE and exposed to X-ray film. The labeled complex containing the ligand-receptor can be excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

The receptor may be utilized to identify or screen agonists and antagonists to the polypeptide of the present invention. Agonists and antagonists can be used to enhance and interfere, respectively, with the function of MEC. As an example, a mammalian cell or membrane preparation expressing a MEC receptor is contacted with a compound of interest. The ability of the compound to generate a response of a known second messenger system following interaction with the MEC receptor is then measured. Such second messenger systems include but are not limited to, cAMP guanylate cyclase, ion channels or phosphoinositide hydrolysis. The ability of a compound to bind the MEC receptor and elicit a second messenger response identifies that compound as an agonist. A compound which binds but does not elicit a second messenger response identifies that compound as an antagonist. Antagonists can be employed, among other uses, to treat inflammation by preventing the attraction of monocytes to a wound or a site of trauma, and to regulate normal macrophage populations.

Antagonists can be negative dominant mutants of the MEC polypeptide. A negative dominant mutant of the polypeptide of the present invention binds to the MEC receptor but fails to activate cells (leukocytes) to which it binds. An assay to detect negative dominant mutants of the polypeptide of the present invention is an in vitro chemotaxis assay wherein a multiwell chemotaxis chamber equipped with polyvinylpyrrolidone-free polycarbonate membranes is used to measure the chemoattractant ability of the MEC polypeptide for leukocytes in the presence and absence of potential antagonist or agonist molecules.

Other useful antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251:1360 (1991)), thereby preventing transcription and the production of the MEC polypeptide. The antisense RNA oligonucleotide hybridizes to the mRNA in vivo and blocks translation of the mRNA molecule into the MEC polypeptide (Antisense-Okano, J. Neurochem., 56:560 (1991); Oligodeoxynucleotides as Antisense Inhibitors of Gene Expression, CRC Press, Boca Raton, Fla. (1988)). Alternatively, an antisense agent hybridizes to the mRNA in vivo and causes degradation of the hybridized mRNA, thereby preventing transcription. The antisense agents can be delivered to cells such that the antisense RNA or DNA may be expressed in vivo to inhibit production of the polypeptide of the present invention.

Yet other antagonists include a small molecule which binds to and occupies the active site of the polypeptide thereby making the catalytic site inaccessible to substrate such that normal biological activity is prevented. Examples of small molecules include but are not limited to small peptides or peptide-like molecules.

The polypeptides, and agonists and antagonists of the present invention may be employed in combination with a suitable pharmaceutical carrier. Such compositions comprise a therapeutically effective amount of the polypeptide or agonist or antagonist, and a pharmaceutically acceptable carrier or excipient. Such a carrier includes but is not limited to saline, buffered saline, dextrose, water, glycerol, ethanol, and combinations thereof. The pharmaceutical compositions should suit the mode of administration.

The pharmaceutical compositions may be administered in a convenient manner such as by the oral, topical, parenterally, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, and the like.

The MEC polypeptide can be produced by well known methods of recombinant DNA technology. MEC may be expressed in a variety of host cells, either prokaryotic or eukaryotic. Cells transformed with DNA encoding MEC may be cultured under conditions suitable for the expression of the MEC and the recovery of the protein from the cell culture. MEC produced by a recombinant cell may be secreted or may be contained intracellularly, depending on the particular genetic construction used. In general, it is more convenient to prepare recombinant proteins in secreted form. Suitable expression hosts include but are not limited to mammalian cells such as Chinese Hamstar Ovary and human 293 cells, insect cells such as Sf9 cells, yeast cells such as *Saccharomyces cerevisiae*, and bacteria such as *E. coil*. For each of these cell systems, a useful expression vector may also include an origin of replication to allow propagation in bacteria and a selectable marker such as the β-lactamase antibiotic resistance gene to allow selection in bacteria. In addition, the vectors may include a second selectable marker such as the neomycin phosphotransferase gene to allow selection in transfected eukaryotic host cells. Vectors for use in eukaryotic expression hosts may require RNA processing elements such as 3' polyadenylation sequences. The vector may also contain promoters or enhancers which increase gene expression. Such promoters are host specific and include MMTV, SV40, or metallothionine promoters for CHO cells; trp, lac, tac or T7 promoters for bacterial hosts, or alpha factor, alcohol oxidase or PGH promoters for yeast. Transcription enhancers, such as the RSV enhancer, may be used in mammalian host cells. Once homogeneous cultures of recombinant cells are obtained through standard culture methods, large quantities of recombinantly produced MEC can be recovered from the conditioned medium and analyzed using chromatographic methods known in the art.

The polypeptide of the present invention include the polypeptide of SEQ ID NO:2 as well as polypeptides which have at least 70%, more preferably at least 90%, most preferably at least 95%, identity to the polypeptide of SEQ ID NO:2. The invention also includes portions or fragments of the polypeptide having at least 30 amino acids of polypeptide SEQ ID NO:2.

In addition to recombinant production, MEC fragments may be produced by direct peptide synthesis using solid-phase techniques. For example, Applied Biosystems 431A Peptide Synthesizer (Foster City, Calif.) can be used to synthesize MEC or fragments thereof. Various fragments of MEC may be chemically synthesized separately and combined using chemical methods to produce full length MEC.

Antibodies of MEC may be produced by inoculating an appropriate animal with the MEC polypeptide or an epitope thereof. An antibody is specific for MEC if the antibody is produced against all or part of the MEC polypeptide and binds to all or part of the protein. Induction of antibodies includes not only the stimulation of an immune response by injection into animals, but also analogous steps in the production of synthetic antibodies or other specific-binding molecules such as the screening of recombinant immunoglobulin libraries (cf Orlandi et al (1989) PNAS 86: 3833–3837, or Huse et al (1989) Science 256: 1275–1281) or the in vitro stimulation of lymphocyte populations. MEC for use in the induction of antibodies do not need to have biological activity; however, it must have immunogenic activity. Peptides for use in the induction of MEC-specific antibodies should mimic a portion of the amino acid sequence of MEC and may contain the entire amino acid sequence of the naturally occurring MEC. Short stretches of MEC amino acid may be fused with those of another protein such as keyhole limpet hemocyanin and the chimeric molecule used for antibody production.

MEC antibodies are useful for diagnosis and prognosis of prepathologic conditions, and chronic or acute diseases which are characterized by differences in the expressed level of MEC. Diagnostic and prognostic tests for MEC include methods utilizing the antibody and a label to detect MEC in human body fluids, tissues or extracts of such tissues. The polypeptides and antibodies of the present invention may be used with or without modification. Frequently, the polypeptides and antibodies will be labeled by joining them, either covalently or noncovalently, with a substance which provides for a detectable signal. A wide variety of labels and conjugation techniques are known and have been reported extensively in both the scientific and patent literature. Suitable labels include radionudides, enzymes, substrates, cofactors, inhibitors, fluorescent agents, chemiluminescent agents, magnetic particles and the like.

The present invention further provides methods of screening for drugs or any other agents which can affect inflammation and disease, e.g., tumor. These methods include the steps of contacting such an agent with a MEC polypeptide or fragment thereof and assaying for the presence of a complex between the agent and the MEC polypeptide or fragment, or for the presence of a complex between the MEC polypeptide or fragment and the cell, by methods well known in the art. In such competitive binding assays, the MEC polypeptide or fragment is typically labeled. After suitable incubation, free MEC polypeptide or fragment is separated from the bound polypeptide or fragment, and the amount of free or uncomplexed label is a measure of the ability of the particular agent to bind to MEC or to interfere with the MEC/cell complex.

Another technique for drug screening provides high throughput screening for compounds having suitable binding affinity to the MEC polypeptides. Large numbers of different small peptide test compounds are synthesized on a solid substrate, such as plastic pins or some other surface. The peptide test compounds are reacted with MEC polypeptide and washed. Bound MEC polypeptide is then detected by methods well known in the art. Purified MEC can also be coated directly onto plates for use in the aforementioned drug screening techniques. In addition, non-neutralizing antibodies can be used to capture the peptide and immobilize it on the solid support.

The present invention also provides a diagnostic or prognostic assay for detecting altered levels of the polypeptide of the present invention in various tissues since a suppressed-expression of the proteins compared to normal control tissue samples can detect the presence of tumor. Assays used to detect levels of the polypeptide of the present invention in a sample derived from a host are well-known to those of skill in the art and include radioimmunoassays, competitive-binding assays, in situ immuno histochemistry, Western Blot analysis and preferably an ELISA assay. An ELISA assay has an initially step of preparing an antibody specific to the MEC antigen, preferably a monoclonal antibody. In addition, a reporter antibody is prepared against the monoclonal antibody. To the reporter antibody, a detectable reagent such as radioactivity, fluorescence or a peroxidase enzyme is attached. For example, a sample is removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attached to any of the polypeptide of the present invention attached to the polystyrene dish. All unbound monoclonal antibody is washed out with buffer. The reporter antibody linked to horseradish peroxidase is now placed in the dish resulting in binding of the reporter antibody to any monoclonal antibody bound to the polypeptide of the present invention. Unattached reporter antibody is then washed out. Peroxidase substrates are then added to the dish and the amount of color developed in a given time period is a measurement of the amount of the polypeptide of the present invention present in a given volume of patient sample when compared against a standard curve.

Our data clearly demonstrate that a primary site of expression of the described chemokine is the luminal epithelial cells of the mammary gland, the cell type from which the vast majority of breast cancers arise. The expression of this chemokine is dramatically and uniformly down-regulated in tumors of the breast compared to the normal glandular epithelium, suggesting that sustained expression of the chemokine is inconsistent with the ability of mammary epithelial cells to contribute to primary tumors in vivo and/or proliferate in an unregulated fashion during the process of tumorigenesis. Thus, the data in the present application suggest that the presence of the MEC protein may be inhibitory to the unregulated proliferation of breast tumors and supports the hypothesis that exogenous administration of the MEC protein or small molecule agonists or antagonists may serve as a potential therapy for the treatment of breast cancer. In addition, the clear observation that MEC expression, as detected by in situ hybridization using a MEC-specific riboprobe, clearly distinguishes mammary tumor cells from normal ductal epithelial cells, even those normal cells adjacent to a tumor, directly demonstrates the utility of MEC expression as an in situ diagnostic marker.

The chemokine of the present invention having the nucleotide and polypeptide sequences of FIG. 1 can be utilized for various purposes including diagnosis, prognosis and treatment of human diseases, e.g., tumors and inflammation. The invention is further described by reference to the following examples. These examples are provided for illustration purposes and are not intended to be limiting.

EXAMPLES

The following procedures were used to conduct the examples.

Expression Analysis by PCR

For analysis of tissue specific expression by the polymerase chain reaction (PCR), the following primers were synthesized: 5'-ctgatcgaacagcctcacttgtgttg-3' and 5'-ctgacacagattcttctgcgcttgac-3'. PCR was carried out utilizing various commercially available cDNAs (Clontech) as template using the Advantage 2 PCR kit (Clontech) under the following conditions: 1 cycle of 94° C.×2 min, 33 cycles of 94° C.×30 seconds, and 68° C.×1 min. The 276 base pair product was verified by subsequent cloning into pCR BluntII-TOPO (Invitrogen) and sequencing. This 276-base pair fragment was used subsequently as a probe in all hybridization experiments.

Generation of Radiolabelled Probes

The 276-base pair fragment was excised from pCR BluntII-TOPO using EcoR1 and gel purified using the Quiaquick Gel Extraction Kit (Qiagen), and subsequently radioactively labeled by random priming using High Prime (Roche Biochemical) and alpha-$^{32}$P dCTP (New England Nuclear).

Northern Blotting and Hybridization

For Northern blotting, 15 micrograms of total RNA from various human tissues (Clontech) was electrophoresed on a 1.0% agarose-formaldehyde gel and transferred to a positively charged nylon membrane, and RNA was immobilized by UV-crosslinking. For analysis of gene expression in human mammary tumor and control samples, a commercially available Northern blot was purchased (Invitrogen). Hybridization was carried out at 60° C. in ExpressHyb hybridization solution (Clontech, Inc.) for two hours and washed subsequently at high stringency. Following hybridization, membranes were exposed to Kodak X-Omat x-ray film at −70° C. or subjected to phosporimager analysis (Molecular Dynamics). All membranes were stripped by boiling for 10 minutes in boiling 0.5% SDS and reprobed with a β-actin cDNA probe (Clontech).

Expression of Recombinant MEC

For the generation of epitope tagged recombinant protein, the following primers were used: 5'-ttgctgtcagtgccagtaggccaggca-3' and 5'-aatcttctagagcctccataaggagttttatggccgtatg-3'. The primers were used to amplify the coding region of MECR using Advantage-2 PCR kit (Clontech), and the product was then cloned into the EcoRV and XbaI sites of the vector pcDNA/3.1/Myc-His+ Version A (Invitrogen). The resulting plasmid was sequence verified to encode a protein that represented the entire coding region of MECR fused in frame to the c-myc epitope (EQKLISEEDL) and 6×H is tag lying downstream of the CMV promoter.

Cell Lines

MD-MBA-435, MD-MBA-231, 293, and T47-D cells were obtained from the American Type Culture Collection and maintained in Dulbecco's Modified Eagle Medium supplemented with 10% fetal bovine serum and antibiotics. T47-D cells were additionally supplemented with 0.02 mg/ml bovine insulin. Human mammary epithelial cells (Clonetics) were maintained according to the supplier's recommendations. All cells were maintained in a humidified incubator with 5% $CO_2$ at 37° C.

Transfection and Recombinant Protein Detection (Western Blot)

Cells were transfected using Geneporter Reagent (Gene Therapy Systems) according to the manufacturer's directions. For analysis of protein expression, transfected 293 cells were incubated in medium containing 0.2% fetal bovine serum and harvested after 48-72 hours. Cell supernatant was collected and cytosolic protein was extracted by lysis in buffer containing 50 mM Tris-HCl pH 8.0, 150 mM NaCl, 1% Igepal CA-360, 0.1% sodium dodecyl sulfate, and 1 ug/ml aprotinin. Proteins were electrophoresed on a 16.5% Tris-Tricine SDS-PAGE gel and transferred to PVDF membrane (Bio-Rad).

For the detection of recombinant protein, membranes were blocked for 1 hour in 25 mg/ml Blocker BSA (Pierce) in Tris buffered saline (TBS). The membranes were then incubated in monoclonal antibody 9E10 ascites (Sigma-Aldrich) which recognizes the c-myc epitope tag at a dilution of 1:250 in TBS with the addition of 0.05% Tween-20 (TBST) for 1 hour. After washing extensively in TBST, a goat anti-mouse secondary antibody coupled to horseradish peroxidase was added at a dilution of 1:40,000 in TBST and incubated for 1 hour. After washing in TBST, the signal was detected using Supersignal West Pico Chemiluminescent Detection System (Pierce) and exposed to Kodak X-Omat x-ray film.

In situ Hybridization of Paraffin-Embedded Tissue For in situ hybridization studies, a 396-bp fragment encompassing the entire coding region of MEC was generated using the primers 5'-ttgctgtcagtgccagtagggcaggc-3' (sense) and 5'-agcctccataaggagttttatggccgtatgt-3' (antisense) and cloned in to pCR-BluntII. MEC cRNA riboprobes were transcribed in vitro with SP6 (antisense) and T7 (sense) RNA polymerases in the presence of $^{35}$S-uridine 5' triphosphate. After transcription, the probes were column purified and electrophoresed onto a 5% polyacrylamide gel to confirm size and purity. All in situ hybridization studies were performed by an outside contractor (Lifespan Biosciences Inc., Seattle, Wash.) as directed by the inventors. Serial tissue sections were carefully selected from archival samples to ensure matched normal tissue was available for all tumor tissue. All tumor tissue had been previously identified as either infiltrating ductal carcinoma or infiltrating ductolobular carcinoma by histopathological analysis. Tissue sections were treated with Proteinase K and hybridized with the probes at approximately $7.0 \times 10^7$ dpm/ml for 18 h at 55° C. Following hybridization, the slides were treated with RNAse A and washed in 0.1×SSC at 55° C. for 2 h. The slides were then coated with emulsion (NTB-2, Kodak), exposed for 4 days at 4° C., and developed using Kodak D-19 developer and fixer (Kodak). Slides were counterstained with hematoxylin and eosin, and photographed with a Nikon camera linked to a Sony Digital Photocamera.

Example 1

An cDNA clone (ID 3778188) from Incyte Pharmaceuticals, Palo Alto, Calif., was obtained and sequenced by ACGT, Inc. The nucleotide sequence was examined for chemokine-like open reading frames (ORF). The ORF of FIG. 1 was the only one within this cDNA.

Example 2

The polynucleotide sequence of Example 1 was cloned upstream and in frame from a myc/his epitope tag in a mammalian expression vector, pcDNA myc/his. This vector was transfected into human 293 cells expression of the tagged protein examined by Western blot analysis. Protein was isolated from either cell pellets or from the culture supernatants. The tagged protein was readily detected in the supernatants indicating that the protein was secreted. The Western blot analysis demonstrated that the chemokine like ORF encodes a secreted factor and the predicted signal sequence in the 3778188 cDNA is functional.

Example 3

Levels of mec RNA were examined by RT-PCR from a variety of tissues, including breast, lung, colon, prosate, colon, ovary and pancreas tissues, which were obtained from Clontech, Inc. The largest signal was detected using mRNA from mammary gland with less signal appearing in pancreas and thymus.

The PCR product was clearly derived from cDNA and not genomic DNA as PCR using genomic DNA produced a larger intron containing band. The genomic structure for this region of MEC was determined by searching the genomic databases, i.e., Celera and public Genomic databases, and an intron was identified between the coding region amplified by the chosen PCR primers.

To confirm the RT-PCR results, the 3778188 sequence was used on a Northern blot of tissue mRNA. Significant levels of hybridizing mRNA were detected only in mammary gland, while the other tissues contained either very low or undetectable levels of hybridizing mRNA. These experiments demonstrate that the 027681 sequence is highly enriched in mammary gland; thus the gene has been termed MECR for Mammary Gland Enriched Chemokine Related sequence.

Example 4

The expression levels of mec were examined in normal and transformed mammary tumor epithelial cells by Northern blot analysis. Carcinoma mammary cell lines MD-MBA231, MD-MBA435 and T47D were obtained from ATCC. MEC was expressed in the tumor lines but at lower levels. There was also very little expression in primary human mammary epithelial cells.

Expression of MEC was also compared in mRNA prepared from surgically removed primary tumors and adjacent normal tissue. Four pairs of matched tumor and normal mammary gland RNA were examined. MEC mRNA was detected in similar high levels in all normal mammary gland but was very low or undetectable in all examined tissues. Thus, MEC expression is extinguished in many tumors and loss of MEC expression is believed to be a major distinguishing factor between tumors and normal mammary gland.

Example 5

In order to identify expression of MEC on a cellular level, paraffin-embedded archival samples of normal mammary tissue was subjected to in situ hybridization with antisense and sense MEC riboprobes. In situ hybridizations were carried out using an antisense MEC riboprobe hybridized to paraffin sections of normal mammary gland from an 18 year old female undergoing reduction mammoplasty. The antisense probe showed moderate hybridization signals within lobular epithelium and ductal epithelium. In general, myoepithelial cells and basal epithelium appeared less strongly positive than did the luminal epithelial cells. Stromal fibroblasts, adipocytes, and endothelial cells were uniformly negative for hybridization. Similar specific staining for MEC in mammary epithelial cells was seen in nine independent normal mammary samples. The hybridization signal was shown to be specific as the sense control riboprobe produced only faint signals across the tissues tested that were not localized to any specific cell type These data demonstrate that MEC expression is highly restricted to mammary epithelial cells.

In situ hybridization was also performed on breast tumors along with normal adjacent tissue derived from the same patients. The antisense probe showed moderate to strong signal in normal epithelium and hyperplastic epithelium lining lobules and ducts; normal breast tissue from a 62 year old female hybridized with antisense probe showed MEC positive cells in the ductal epithelium and breast tissue from a 61 year old hybridized with antisense probe demonstrated expression of MEC in normal ducts, with little or no signal detected in the adjacent nests of invasive ductal carcinoma. In infiltrating ductal and intraductal carcinomas, the signal intensity was significantly less intense and less uniform across the nests of carcinoma; invasive ductal carcinoma tissue from the 62 year old female patient also showed no detectable MEC expression.

A total of nine patients was examined, comprised of four patients diagnosed with infiltrating ductal carcinoma and five patients diagnosed with invasive ductolobular carcinoma. While all nine of the patient samples displayed differential expression of MEC with regard to normal ductal epithelium versus tumor tissue, there was some heterogeneity of signal intensity between normal ductal epithelium of different patients. However, in all cases MEC expression was consistently lost or highly reduced in mammary tumor epithelial cells in vivo.

What is claimed is:

1. A method for detecting the presence of a breast tumor comprising the steps of:
    a) providing a probe, wherein said probe comprises at least 10 consecutive nucleotides in length, and which hybridizes to a nucleic acid sequence consisting of SEQ ID NO: 1;
    b) contacting a breast sample with said probe and
    c) quantifying the level of hybridization of said probe wherein reduced levels of hybridization to a sequence comprising SEQ ID NO: 1 compared to control levels in surrounding breast tissue samples indicates the presence of a breast tumor.

2. A method for detecting a breast tumor in a subject characterized by a reduced level of expression of Mammary gland Enriched Chemokine (MEC). wherein MEG is encoded by SEQ ID NO: 1, comprising: (a) contacting a breast sample with a probe that hybridizes to a nucleic acid sequence consisting of SEQ ID NO: 1 or to the full complement thereof; and (b) measuring the hybridization level of said probe to a polynucleotide comprising SEQ ID NO: 1 or to a polynucleotide comprising a full complement of SEQ ID NO: 1, wherein a reduction or loss of hybridization levels compared to hybridization levels in breast samples without tumors or to levels in tissue surrounding the location of a breast tumor indicates the presence of a breast tumor in said subject.

3. The method of claim 2, wherein said measuring step comprises Northern blot analysis, polymerase chain reaction (PCR), reverse transcriptase PCR, or in situ hybridization.

4. The method of claim 3 wherein said probe comprises a sequence of at least 10 consecutive nucleotides.

5. The method of claim 3 wherein said probe comprises a sequence of at least 20 consecutive nucleotides.

6. The method of claim 3 wherein said probe comprises a sequence of at least 50 consecutive nucleotides.

7. A method for detecting a breast tumor in a patient, comprising the steps of:
    a) providing a probe, the nucleotide sequence of which consists of SEQ ID NO: 1 or a fragment thereof of at least 10 consecutive nucleotides;
    b) contacting said probe to a sample of breast tissue or breast tissue extract from said patient, wherein the sampled breast tissue is suspected of having a tumor, to permit hybridization of said probe to mRNA encoding a protein encoded by SEQ ID NO: 1 and
    c) quantifying the level of hybridization of said probe to said mRNA wherein reduction or loss of hybridization levels in the sample compared to levels of hybridization of said probe to said mRNA in breast tissue adjacent to the location of said sample indicates the presence of a breast tumor in said patient.

* * * * *